(12) United States Patent
Zhang et al.

(10) Patent No.: US 11,965,845 B2
(45) Date of Patent: Apr. 23, 2024

(54) DEVICE AND METHOD FOR MEASURING FLUID SATURATION IN NUCLEAR MAGNETIC RESONANCE ON-LINE DISPLACEMENT

(71) Applicants: Institute of Geology and Geophysics, Chinese Academy of Sciences, Beijing (CN); Northeast Petroleum University, Daqing (CN)

(72) Inventors: Likuan Zhang, Beijing (CN); Xiaorong Luo, Beijing (CN); Jianzhao Yan, Daqing (CN); Yuhong Lei, Beijing (CN); Ming Cheng, Beijing (CN); Naigui Liu, Beijing (CN)

(73) Assignees: Institute of Geology and Geophysics, Chinese Academy of Sciences, Beijing (CN); Northeast Petroleum University, Daqing (CN)

( * ) Notice: Subject to any disclaimer, the term of this patent is extended or adjusted under 35 U.S.C. 154(b) by 56 days.

(21) Appl. No.: 17/860,570

(22) Filed: Jul. 8, 2022

(65) Prior Publication Data
US 2023/0045602 A1    Feb. 9, 2023

(30) Foreign Application Priority Data

Jul. 8, 2021   (CN) .......................... 202110774827.8

(51) Int. Cl.
*G01N 24/08*    (2006.01)
*G01N 15/08*    (2006.01)
(Continued)

(52) U.S. Cl.
CPC ......... *G01N 24/081* (2013.01); *G01N 15/088* (2013.01); *G01N 24/082* (2013.01);
(Continued)

(58) Field of Classification Search
CPC .... G01N 24/08; G01N 24/081; G01N 24/082; G01N 24/088; G01N 15/08;
(Continued)

(56) References Cited

U.S. PATENT DOCUMENTS

2017/0115242 A1   4/2017   Kwak et al.
2020/0057172 A1   2/2020   Alharbi et al.

FOREIGN PATENT DOCUMENTS

CN    101967970 A    2/2011
CN    104854470 A    8/2015
(Continued)

OTHER PUBLICATIONS

English translation of CN 105891248 to Li (Year: 2016).*
(Continued)

*Primary Examiner* — Steven L Yeninas
*Assistant Examiner* — Rahul Maini
(74) *Attorney, Agent, or Firm* — Nutter McClennen & Fish LLP

(57) ABSTRACT

The present invention provides a device and a method for measuring fluid saturation in nuclear magnetic resonance (NMR) on-line displacement, the method comprising: measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum; measuring a nuclear magnetic resonance (NMR) T2 spectrum of a process in which the core to be measured is converted from a saturated displaced phase fluid into a displacing phase fluid to generate a displacement process T2 spectrum; generating the fluid saturation of the on-line displacement system in real time according to the generated calibrated T2 spectrum and the displacement process T2 spectrum. The present inven-
(Continued)

measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum — 100 measuring a nuclear magnetic resonance (NMR) T2 spectrum of a process in which the core to be measured is converted from a saturated displaced phase fluid into a displacing phase fluid to generate a displacement process T2 spectrum — 200 generating the fluid saturation of the on-line displacement system in real time according to the calibrated T2 spectrum and the displacement process T2 spectrum — 300 tion achieves the purpose of improving measurement precision of fluid saturation in the on-line displacement process.

7 Claims, 10 Drawing Sheets

(51) Int. Cl.
  *G01R 33/44* (2006.01)
  *G01V 3/32* (2006.01)
  *G01V 3/38* (2006.01)
(52) U.S. Cl.
  CPC .............. *G01R 33/448* (2013.01); *G01V 3/32* (2013.01); *G01V 3/38* (2013.01)
(58) Field of Classification Search
  CPC ........... G01N 15/0806; G01N 15/0833; G01N 15/0846; G01N 15/088; G01N 15/0893; G01R 33/44; G01R 33/448; G01V 3/32; G01V 3/38
  USPC ....................................................... 324/303
  See application file for complete search history.

(56) References Cited

FOREIGN PATENT DOCUMENTS

| CN | 105891248 | A | * | 8/2016 | | |
| CN | 105891248 | A | | 8/2016 | | |
| CN | 109444201 | A | | 3/2019 | | |
| CN | 110398510 | A | | 11/2019 | | |
| CN | 111220639 | A | | 6/2020 | | |
| CN | 111878050 | A | | 11/2020 | | |
| CN | 112213345 | A | | 1/2021 | | |
| CN | 112881472 | A | * | 6/2021 | ............ | G01N 15/08 |
| CN | 112881472 | A | | 6/2021 | | |

OTHER PUBLICATIONS

English translation of CN 112881472 to Dai (Year: 2021).*
Fang Tao et al., Study on Migration Characteristics of Tight Sandstone Gas Based on Nuclear Magnetic Resonance, Journal of Gansu Sciences, vol. 29 No.4, Aug. 2017, (6 pages).
Jianzhao Yan et al., Testing oil saturation distribution in migration paths using MRI, Journal of Petroleum Science and Engineering, Mar. 2012, (9 pages).
Shuo Li et al., Study on the Recovery of Oil Saturation in Cores Using Nuclear Magnetic Resonance Technology, Journal of Oil and Gas Technology, vol. 29 No.2, Apr. 2007, (4 pages).
Yongchao Zhang et al., Experimental investigation on oil migration and accumulation in tight sandstones, Journal of Petroleum Science and Engineering, Oct. 2017, (31 pages).
Fagn Tao et al., Study on Migration Characteristics of Tight Sandstone Gas Based on Nuclear Magnetic Resonance, Journal of Gansu Sciences, Aug. 2017, No. 4, (6 pages).
First Office Action and search report dated Jul. 20, 2022 for counterpart Chinese patent application No. 202110774827.8, along with machine EN translation downloaded from EPO (19 pages).
Office Action and Search Report for Chinese patent application No. 202110774827.8 dated Dec. 21, 2022, along with English translation (9 pages).

* cited by examiner

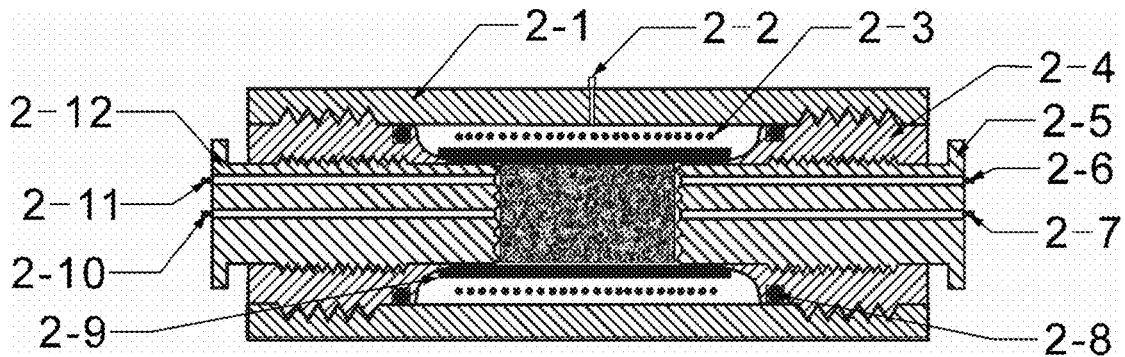

FIG.2

```
measuring a nuclear magnetic resonance (NMR) T2 spectrum
under the dead volume filling of the on-line displacement system
as displacing phase fluid and the core to be measured as saturated      ──  100
nuclear magnetic detection phase fluid to generate a calibrated T2
                            spectrum
```

```
measuring a nuclear magnetic resonance (NMR) T2 spectrum of a
  process in which the core to be measured is converted from a
saturated displaced phase fluid into a displacing phase fluid to       ──  200
         generate a displacement process T2 spectrum
```

```
generating the fluid saturation of the on-line displacement system
   in real time according to the calibrated T2 spectrum and the       ──  300
              displacement process T2 spectrum
```

FIG.3

```
┌─────────────────────────────────────────────────────┐
│  measuring a nuclear magnetic resonance (NMR) T2    │
│  spectrum under the dead volume filling of the      │
│  on-line displacement system as displacing phase    │
│  fluid and the core to be measured that is          │──── 400
│  saturated with the displaced phase fluid, to       │
│  generate an initial T2 spectrum                    │
└─────────────────────────────────────────────────────┘
                          │
                          ▼
┌─────────────────────────────────────────────────────┐
│  correcting the fluid saturation of the on-line     │
│  displacement system according to the initial T2    │──── 500
│  spectrum, the calibrated T2 spectrum and the       │
│  displacement process T2 spectrum                   │
└─────────────────────────────────────────────────────┘
```

FIG.8

```
┌─────────────────────────────────────────────────────┐
│  saturating the core to be measured with the        │
│  displaced phase fluid and filling it into a core   │──── 401
│  holder                                             │
└─────────────────────────────────────────────────────┘
                          │
                          ▼
┌─────────────────────────────────────────────────────┐
│  applying a predetermined confining pressure to the │
│  core holder by means of a ring pressure pump and a │──── 402
│  pressure gauge on the third pipe                   │
└─────────────────────────────────────────────────────┘
                          │
                          ▼
┌─────────────────────────────────────────────────────┐
│  opening the valves on the liquid discharge end     │
│  evacuation pipe and the liquid inlet end           │
│  evacuation pipe respectively, and filling the      │──── 403
│  displacing phase fluid into the dead volume of the │
│  on-line displacement system                        │
└─────────────────────────────────────────────────────┘
                          │
                          ▼
┌─────────────────────────────────────────────────────┐
│  closing the valves on the liquid discharge end     │
│  evacuation pipe and the liquid inlet end           │──── 404
│  evacuation pipe                                    │
└─────────────────────────────────────────────────────┘
                          │
                          ▼
┌─────────────────────────────────────────────────────┐
│  performing nuclear magnetic resonance (NMR)        │
│  scanning on the displacing phase fluid in the dead │──── 405
│  volume and the core to be measured to generate the │
│  initial T2 spectrum                                │
└─────────────────────────────────────────────────────┘
```

FIG.9

DEVICE AND METHOD FOR MEASURING FLUID SATURATION IN NUCLEAR MAGNETIC RESONANCE ON-LINE DISPLACEMENT

TECHNICAL FIELD

The invention relates to the field of petroleum exploration and development, in particular to a core parameter measurement technology, and specifically to a device and a method for measuring fluid saturation in nuclear magnetic resonance (NMR) on-line displacement.

BACKGROUND

Fluid saturation refers to the percentage of the volume of a saturated fluid in a porous medium to the total pore volume. Saturation is an important parameter involved in the estimation of oil and gas resources, and it is also an important factor affecting seepage law of oil, gas and water in rocks. Conventional methods of measuring fluid saturation include distillation extraction, dry distillation extraction, and chromatography. Measurement of saturation by these methods inevitably destroys the distribution of fluid in a pore medium. Hence, these conventional methods are not capable of measuring fluid saturation during displacement.

Nuclear magnetic resonance (NMR) technology can be used to measure the saturation without destroying the fluid distribution in the porous medium, that is, non-destructive measurement. The document *Testing oil saturation distribution in migration paths using MRI* discloses a technology for measuring oil saturation using a nuclear magnetic resonance imaging technology. However, due to the limitation of resolution, nuclear magnetic resonance imaging is only suitable for measuring fluid saturation in loose porous medium with excellent permeability.

Fluid saturation in actual cores can be measured using a nuclear magnetic resonance relaxation spectrum, and the basic idea is to calculate the saturation of different fluids by counting the accumulated nuclear magnetic resonance signals corresponding to different fluids and combining with hydrogen index correction. The difficulty of this method is that the NMR signal distribution regions of different fluids often overlap in the NMR relaxation spectrum. In the paper *Study On Oil Saturation Recovery of Core Using NMR Technology*, it is proposed that by soaking the core in the manganese water, the water phase signal can be shielded by the diffusion of manganese ions into the core, and the fluid saturation is determined by comparing the change of transverse relaxation spectrum (T2) before and after soaking in manganese. However, due to the influence of wettability, spontaneous imbibition occurs in the process that the rock is soaked in manganese, and the fluid saturation in the core is changed.

The on-line measurement of fluid saturation during displacement or filling has also attracted the attention of many researchers. The document *Experimental Investigation on Oil Migration and Accumulation in Tight Sandstones* discloses that an oil-water separation metering device is installed at the terminal of a displacement process, by which the oil saturation of the core is calculated by metering the volume of oil and water injected into the core and discharged from the core respectively, but the fluid volume in the diversion trench and the outflow pipeline of the core holder plug cannot be metered, called "dead volume", which brings an inevitable system error to the measurement of fluid saturation, and in particular in low permeability and tight cores, this error can be greatly exaggerated and can even lead to misperception due to the very limited amount of saturated fluid in the core. The nuclear magnetic resonance (NMR) relaxation spectrum can be used to measure the fluid saturation in the displacement process on line by combining the NMR and the displacement system. The patent application with the publication number CN111220639A, Method and Device for Measuring Gas Saturation of Core During Gas Flooding Based on Nuclear Magnetic Resonance, and Study On Gas Migration Characteristics of Tight Sandstone Based on Nuclear Magnetic Resonance Technology all propose that the fluid saturation in the gas flooding process is measured by using the nuclear magnetic resonance on-line displacement system; and the patent application with the publication number CN111878050A discloses a method for enhanced oil recovery in tight oil/water flooding developed by nuclear magnetic resonance (NMR) on-line. In the above-mentioned nuclear magnetic resonance (NMR) on-line displacement system, only the NMR scanning of the fluid inside the effective magnetic field is taken into consideration, and the influence of the dead volume of the outflow pipeline outside the magnetic field can be eliminated. However, in the magnetic field, the corresponding dead volume of the outflow pipeline and the diversion trench of the holder plug still exist, which will still lead to systemic errors.

In summary, there is an urgent need in the related art for a method and a device that can measure fluid saturation of an on-line displacement system accurately and in real time.

SUMMARY OF THE INVENTION

An embodiment of the present invention provides a device and a method for measuring fluid saturation in nuclear magnetic resonance (NMR) on-line displacement, in which the boundary point between the saturated fluid and the dead volume fluid in T2 spectrum is determined by observing the change characteristics of the T2 spectrum, so that only the saturated fluid signal can be counted, and the influence of the dead volume fluid can be shielded, so as to achieve the purpose of improving measurement precision of fluid saturation in the on-line displacement process.

In an aspect, the embodiment of the present invention provides a device for measuring fluid saturation in nuclear magnetic resonance (NMR) on-line displacement, comprising:

an injection device, an intermediate container, a core holder, and a nuclear magnetic resonance (NMR) instrument, wherein, the injection device is connected to one end of the intermediate container through a first pipe, for injecting fluid into the intermediate container;

the other end of the intermediate container is connected to the core holder by a second pipe, for injecting the fluid into the core in the core holder;

the core holder is located in a central area of the magnetic field of the NMR instrument, for monitoring the NMR signal of the core to be measured;

the core holder includes a sleeve, two fixed plugs, a liquid discharge end movable plug and a liquid inlet end movable plug, wherein, the two fixed plugs are arranged at two ends of the sleeve respectively;

the liquid discharge end movable plug and the liquid inlet end movable plug pass through the fixed plugs and abut against both ends of the core, to fix the core axially;

the liquid discharge end movable plug is provided with an evacuation pipe and a liquid discharge pipe;

the liquid inlet end movable plug is provided with an evacuation pipe and a liquid inlet pipe;

the liquid inlet pipe is connected to the intermediate container through the second pipe.

In an embodiment, the device for measuring fluid saturation in nuclear magnetic resonance (NMR) on-line displacement further comprises a ring pressure pump connected to the core holder through a third pipe.

In an embodiment, the second pipe and the third pipe are provided with pressure gauges respectively, and the third pipe is provided with a valve.

In an embodiment, valves are arranged on portions of the liquid discharge end evacuation pipe and the liquid inlet end evacuation pipe that are located outside the core holder.

In an embodiment, the NMR detection coil of the NMR instrument is built into the core holder.

In another aspect, the embodiment of the present invention provides a method for measuring fluid saturation in nuclear magnetic resonance (NMR) on-line displacement, comprising:

measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum;

measuring a nuclear magnetic resonance (NMR) T2 spectrum of a process in which the core to be measured is converted from a saturated displaced phase fluid into a displacing phase fluid to generate a displacement process T2 spectrum;

generating the fluid saturation of the on-line displacement system in real time according to the calibrated T2 spectrum and the displacement process T2 spectrum, wherein, the dead volume is the sum of the space of a liquid discharge end evacuation pipe, a liquid discharge end liquid discharge pipe, a liquid inlet end evacuation pipe, a liquid inlet end liquid inlet pipe and the space of the diversion trench of the core holder plug;

the nuclear magnetic detection phase fluid is a phase fluid in which the influence of the nuclear magnetic resonance is difficult to eliminate, among the displacing phase fluid and the displaced phase fluid.

In an embodiment, the measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum, includes:

saturating the core to be measured with the nuclear magnetic detection phase fluid and filling it into a core holder;

applying a predetermined confining pressure to the core holder by means of a ring pressure pump and a pressure gauge on the third pipe;

opening the valves on the liquid discharge end evacuation pipe and the liquid inlet end evacuation pipe respectively, and filling the displacing phase fluid into the dead volume of the on-line displacement system;

closing the liquid inlet end evacuation pipe and the valves on the liquid discharge end evacuation pipe;

performing nuclear magnetic resonance (NMR) scanning on the displacing phase fluid in the dead volume and the core to be measured to generate the calibrated T2 spectrum.

In an embodiment, the measuring a nuclear magnetic resonance (NMR) T2 spectrum of a process in which the core to be measured is converted from a saturated displaced phase fluid into a displacing phase fluid to generate a displacement process T2 spectrum, includes:

saturating the core to be measured with the displaced phase fluid and filling it into a core holder;

applying a predetermined confining pressure to the core holder by means of a ring pressure pump and a pressure gauge on the third pipe;

opening the valves on the liquid discharge end evacuation pipe and the liquid inlet end evacuation pipe respectively, and filling the displacing phase fluid into the dead volume of the on-line displacement system;

closing the valves on the liquid discharge end evacuation pipe and the liquid inlet end evacuation pipe;

injecting the displacing phase fluid in an intermediate container into the core to be measured by an injection device;

performing NMR scanning on the displacement process of the core to be measured to generate the displacement process T2 spectrum.

In an embodiment, the generating the fluid saturation of the on-line displacement system in real time according to the calibrated T2 spectrum and the displacement process T2 spectrum, includes:

determining a boundary relaxation time according to the displacement process T2 spectrum, wherein the boundary relaxation time is a time boundary point in the displacement process T2 spectrum that represents the fluid in the core to be measured and represents the dead volume fluid;

determining a true T2 spectrum in the displacement process of the core to be measured according to the boundary relaxation time;

calculating fluid saturation in the displacement process of the core to be measured according to the true T2 spectrum and the calibrated T2 spectrum.

In an embodiment, the determining a boundary relaxation time according to the displacement process T2 spectrum, includes:

obtaining a long relaxation time spectrum thereof according to the displacement process T2 spectrum;

determining an intersection point of increase and decrease of the long relaxation time spectrum;

determining the calibrated T2 spectrum to determine the boundary relaxation time according to a time corresponding to the intersection point.

In an embodiment, the method for measuring fluid saturation in nuclear magnetic resonance (NMR) on-line displacement further comprises: correcting the fluid saturation of the on-line displacement system, including:

measuring a nuclear magnetic resonance (NMR) T2 spectrum under the dead volume filling of the on-line displacement system as displacing phase fluid and the core to be measured that is saturated with the displaced phase fluid, to generate an initial T2 spectrum;

correcting the fluid saturation of the on-line displacement system according to the initial T2 spectrum, the calibrated T2 spectrum and the displacement process T2 spectrum.

In an embodiment, the measuring a nuclear magnetic resonance (NMR) T2 spectrum under the dead volume filling of the on-line displacement system as displacing phase fluid and the core to be measured that is saturated with the displaced phase fluid, to generate an initial T2 spectrum, includes:

saturating the core to be measured with the displaced phase fluid and filling it into a core holder;

applying a predetermined confining pressure to the core holder by means of a ring pressure pump and a pressure gauge on the third pipe;

opening the valves on the liquid discharge end evacuation pipe and the liquid inlet end evacuation pipe respectively, and filling the displacing phase fluid into the dead volume of the on-line displacement system;

closing the valves on the liquid discharge end evacuation pipe and the liquid inlet end evacuation pipe;

performing nuclear magnetic resonance (NMR) scanning on the displacement phase fluid in the dead volume and the core to be measured to generate the initial T2 spectrum.

Thirdly, the embodiment of the present invention provides a system for measuring fluid saturation in nuclear magnetic resonance (NMR) on-line displacement, comprising:

a calibrated T2 spectrum generation unit for measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum;

a displacement T2 spectrum generation unit for measuring a nuclear magnetic resonance (NMR) T2 spectrum of a process in which the core to be measured is converted from a saturated displaced phase fluid into a displacing phase fluid to generate a displacement process T2 spectrum;

a saturation generation unit for generating the fluid saturation of the on-line displacement system in real time according to the calibrated T2 spectrum and the displacement process T2 spectrum, wherein, the dead volume is the sum of the space of a liquid discharge end evacuation pipe, a liquid discharge end liquid discharge pipe, a liquid inlet end evacuation pipe, a liquid inlet end liquid inlet pipe and the space of the diversion trench of the core holder plug;

the nuclear magnetic detection phase fluid is a phase fluid in which the influence of the nuclear magnetic resonance is difficult to eliminate, among the displacing phase fluid and the displaced phase fluid.

In an embodiment, the calibrated T2 spectrum generation unit includes:

a first core saturation module for saturating the core to be measured with the nuclear magnetic detection phase fluid and filling it into a core holder;

a first pressurization module for applying a predetermined confining pressure to the core holder by means of a ring pressure pump and a pressure gauge on the third pipe;

a first dead volume injection module for opening the valves on the liquid discharge end evacuation pipe and the liquid inlet end evacuation pipe respectively, and filling the displacing phase fluid into the dead volume of the on-line displacement system;

a first valve closing module for closing the valves on the liquid discharge end evacuation pipe and the liquid inlet end evacuation pipe;

a calibrated T2 spectrum generation module for performing nuclear magnetic resonance (NMR) scanning on the displacing phase fluid in the dead volume and the core to be measured to generate the calibrated T2 spectrum.

In an embodiment, the displacement T2 spectrum generation unit includes:

a second core saturation module for saturating the core to be measured with the displaced phase fluid and filling it into a core holder;

a second pressurization module for applying a predetermined confining pressure to the core holder by means of a ring pressure pump and a pressure gauge on the third pipe;

a second dead volume injection module for opening the valves on the liquid discharge end evacuation pipe and the liquid inlet end evacuation pipe respectively, and filling the displacing phase fluid into the dead volume of the on-line displacement system;

a second valve closing module for closing the valves on the liquid discharge end evacuation pipe and the liquid inlet end evacuation pipe;

a fluid injection module for injecting the displacing phase fluid in an intermediate container into the core to be measured by an injection device;

a displacement T2 spectrum generation module for performing NMR scanning on the displacement process of the core to be measured to generate the displacement process T2 spectrum.

In an embodiment, the saturation generation unit includes:

a boundary time determination module for determining a boundary relaxation time according to the displacement process T2 spectrum, wherein the boundary relaxation time is a time boundary point in the displacement process T2 spectrum that represents the fluid in the core to be measured and represents the dead volume fluid;

a true T2 spectrum determination module for determining a true T2 spectrum in the displacement process of the core to be measured according to the boundary relaxation time;

a saturation calculation module for calculating fluid saturation in the displacement process of the core to be measured according to the true T2 spectrum and the calibrated T2 spectrum.

In an embodiment, the boundary time determination module includes:

a long relaxation obtaining module for obtaining a long relaxation time spectrum thereof according to the displacement process T2 spectrum;

an intersection point determination module for determining an intersection point of increase and decrease of the long relaxation time spectrum;

a boundary time determination module for determining the calibrated T2 spectrum to determine the boundary relaxation time according to a time corresponding to the intersection point.

In an embodiment, the device for measuring fluid saturation in nuclear magnetic resonance (NMR) on-line displacement further comprises: a saturation correction unit for correcting the fluid saturation of the on-line displacement system, the saturation correction unit including:

an initial T2 spectrum generation module for measuring a nuclear magnetic resonance (NMR) T2 spectrum under the dead volume filling of the on-line displacement system as displacing phase fluid and the core to be measured that is saturated with the displaced phase fluid, to generate an initial T2 spectrum;

a saturation correction module for correcting the fluid saturation of the on-line displacement system according to the initial T2 spectrum, the calibrated T2 spectrum and the displacement process T2 spectrum.

In an embodiment, the initial T2 spectrum generation module includes:
- a third core saturation module for saturating the core to be measured with the displaced phase fluid and filling it into a core holder;
- a third pressurization module for applying a predetermined confining pressure to the core holder by means of a ring pressure pump and a pressure gauge on the third pipe;
- a valve opening module for opening the valves on the liquid discharge end evacuation pipe and the liquid inlet end evacuation pipe respectively, and filling the displacing phase fluid into the dead volume of the on-line displacement system;
- a third valve closing module for closing the valves on the liquid discharge end evacuation pipe and the liquid inlet end evacuation pipe;
- an initial T2 spectrum generation sub-module for performing nuclear magnetic resonance (NMR) scanning on the displacing phase fluid in the dead volume and the core to be measured to generate the initial T2 spectrum.

In a fourth aspect, the present invention provides an electronic device, including a memory, a processor, and a computer program stored on the memory and executable on the processor, wherein when executing the program, the processor implements the steps of the method for measuring fluid saturation in nuclear magnetic resonance (NMR) on-line displacement.

In a fifth aspect, the present invention provides a computer readable storage medium which stores a computer program which, when being executed by a processor, implements the steps of the method for measuring fluid saturation in nuclear magnetic resonance (NMR) on-line displacement.

As can be seen from the above description, the embodiment of the present invention provides a device and a method for measuring fluid saturation in nuclear magnetic resonance (NMR) on-line displacement, the method comprising: measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum; measuring a nuclear magnetic resonance (NMR) T2 spectrum of a process in which the core to be measured is converted from a saturated displaced phase fluid into a displacing phase fluid to generate a displacement process T2 spectrum; generating the fluid saturation of the on-line displacement system in real time according to the generated calibrated T2 spectrum and the displacement process T2 spectrum. Specifically, the invention has the following beneficial effects:

1) By reasonable design and selection, the corresponding T2 spectrum of dead volume fluid has two trends of increasing and decreasing in the process of displacement, the corresponding relaxation time TD at the intersection of two trends is taken as a boundary line. When T2<TD, the core saturated fluid signal is reflected, and when T2>TD, the dead volume fluid signal is reflected. Only the fluid saturation is statistically calculated for the saturated fluid signal, such that the system error caused by the dead volume fluid can be shielded and eliminated, and the accuracy of saturation measurement can be improved, which is especially important for dense and low permeability cores.

2) In the displacement of immiscible two-phase fluid, only one phase fluid generates a NMR signal, and the phase fluid is taken as the analysis object, and the fluid saturation is measured by calibration, which can effectively solve the problem of saturation measurement caused by signal differentiation when the NMR signals of different phase fluids overlap.

BRIEF DESCRIPTION OF THE DRAWINGS

In order to more clearly explain the embodiments of the invention or the technical solution in the prior art, drawings that need to be used in the description in embodiments or the prior art will be simply introduced below, obviously the drawings in the following description are some examples of the invention, for persons ordinarily skilled in the art, it is also possible to obtain other drawings according to these drawings without making creative efforts.

FIG. 2 is a second structural schematic diagram of a device for measuring fluid saturation in nuclear magnetic resonance (NMR) on-line displacement according to an embodiment of the present invention;

FIG. 3 is a first flow schematic diagram of a method for measuring fluid saturation in nuclear magnetic resonance (NMR) on-line displacement according to an embodiment of the present invention;

FIG. 8 is a second flow schematic diagram of a method for measuring fluid saturation in nuclear magnetic resonance (NMR) on-line displacement according to an embodiment of the present invention;

FIG. 9 is a flow schematic diagram of the step 400 of the method for measuring fluid saturation in nuclear magnetic resonance (NMR) on-line displacement according to an embodiment of the present invention;

DETAILED DESCRIPTION OF THE PREFERRED EMBODIMENTS

Hereinafter the technical solution in the embodiments of the present invention will be described clearly and integrally in combination with the accompanying drawings in the embodiments of the present invention, and obviously the described embodiments are merely part of the embodiments, not all of the embodiments. Based on the embodiments of the present invention, all other embodiments that are obtained by persons skilled in the art without making creative efforts fall within the protection scope of the present invention.

Figure 1:
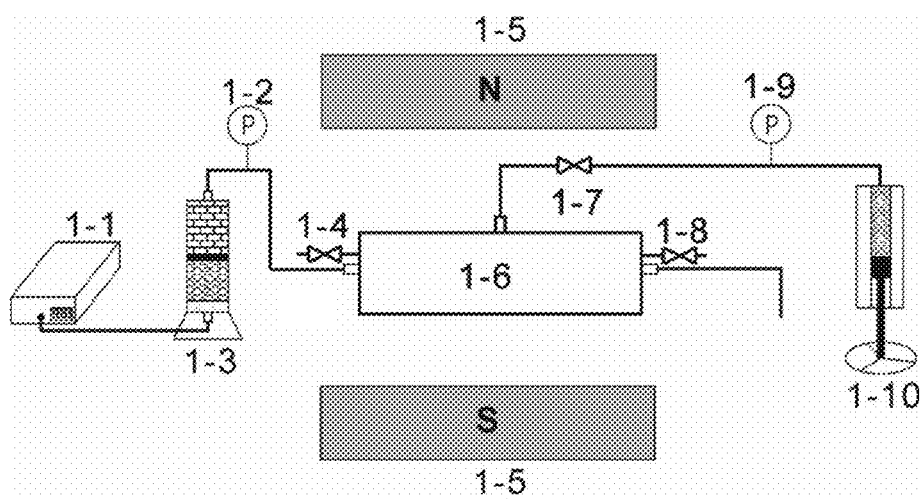
FIG. 1 is a first structural schematic of a device for measuring fluid saturation in nuclear magnetic resonance (NMR) on-line displacement according to an embodiment of the present invention.

An embodiment of the present invention provides a specific embodiment of a device for measuring fluid saturation in nuclear magnetic resonance (NMR) on-line displacement. Referring to FIG. 1, the device specifically includes the following components: an injection device 1-1, an intermediate container 1-3, a core holder 1-6, and a nuclear magnetic resonance (NMR) instrument, wherein, the injection device 1-1 is connected to one end of the intermediate container 1-3 through a first pipe, for injecting fluid into the intermediate container 1-3; the other end of the intermediate container 1-3 is connected to the core holder 1-6 by a second pipe, for injecting the fluid into the core in the core holder 1-6; the NMR instrument is provided near the core holder 1-6 and is used to monitor the NMR signal of the core to be measured. Preferably, a NMR detection coil is built into the core holder 1-6.

Next, referring to FIG. 2, the core holder 1-6 includes: a sleeve 2-1, two plugs (a movable plug 2-5 and a liquid inlet end movable plug 2-12), a liquid discharge end evacuation pipe 2-6, a liquid discharge end liquid discharge pipe 2-7, a liquid inlet end evacuation pipe 2-11 and a liquid inlet end liquid inlet pipe 2-10, wherein the two plugs are arranged at two ends of the sleeve respectively; the liquid discharge end evacuation pipe 2-6 and the liquid discharge end liquid discharge pipe 2-7 pass through the interior of a plug and are connected to the intermediate container 1-3 through a second pipe 1-11; the liquid inlet end evacuation pipe 2-11 and the liquid inlet end liquid inlet pipe 2-10 pass through the interior of the other plug.

Referring to FIG. 1, in an embodiment, the device for measuring fluid saturation in nuclear magnetic resonance (NMR) on-line displacement further comprises a ring pressure pump 1-10, which connected to the core holder 1-6 through a third pipe 1-12.

Referring to FIG. 1, in an embodiment, the second pipe 1-11 and the third pipe 1-12 are provided with pressure gauges 1-2 and 1-9 respectively, and the third pipe 1-12 is provided with a valve 1-7.

Referring to FIG. 1, in an embodiment, valves 1-8 and 1-4 are arranged on portions of the liquid discharge end evacuation pipe 2-6 and the liquid inlet end evacuation pipe 2-11 that are located outside the core holder 1-6.

Referring to FIGS. 1 and 2, in an embodiment, the NMR detection coil (radio frequency coil) 2-3 of the NMR instrument is built into the core holder 1-6. It can be understood that, in order to improve the signal-to-noise ratio of the nuclear magnetic resonance measurement, the radio frequency coil is built in a confinement pressure cavity of the core holder. In order to prevent the measurement effect from being affected by the nuclear magnetic resonance signal generated by the fluid in the confining pressure cavity, the fluid used for filling the confining pressure cavity is fluorocarbon oil without the NMR signal.

As can be seen from the above description, the embodiment of the present invention provides a device for measuring fluid saturation in nuclear magnetic resonance (NMR) on-line displacement, the device comprising: an injection device, an intermediate container, a core holder, and a nuclear magnetic resonance (NMR) instrument, wherein, the injection device is connected to one end of the intermediate container through a first pipe, for injecting fluid into the intermediate container; the other end of the intermediate container is connected to the core holder by a second pipe, for injecting the fluid into the core in the core holder; the NMR instrument is provided near the core holder and is used to monitor the NMR signal of the core to be measured. The core holder includes: a sleeve, two plugs, a liquid discharge end evacuation pipe, a liquid discharge end liquid discharge pipe, a liquid inlet end evacuation pipe and a liquid inlet end liquid inlet pipe, wherein the two plugs are arranged at two ends of the sleeve respectively; the liquid discharge end evacuation pipe and the liquid discharge end liquid discharge pipe pass through the interior of a plug and are connected to the intermediate container through a second pipe; the liquid inlet end evacuation pipe and the liquid inlet end liquid inlet pipe pass through the interior of the other plug. Based on the device for measuring fluid saturation in nuclear magnetic resonance (NMR) on-line displacement provided in the embodiment of the present invention, the invention can solve the problem in the prior art that the system error caused by the dead volume can not be effectively avoided when fluid saturation is measured by the on-line displacement system.

The embodiment of the present invention provides a specific embodiment of a method for measuring fluid saturation in nuclear magnetic resonance (NMR) on-line displacement. Referring to FIG. 3, the method specifically includes:

A step 100 for measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum.

In the step 100, the dead volume is the sum of the space of a liquid discharge end evacuation pipe, a liquid discharge end liquid discharge pipe, a liquid inlet end evacuation pipe, a liquid inlet end liquid inlet pipe and the space of the diversion trench of the core holder plug; the nuclear magnetic detection phase fluid is a phase fluid in which the influence of the nuclear magnetic resonance is difficult to eliminate, among the displacing phase fluid and the displaced phase fluid.

Specifically, a displacing phase fluid, a displaced phase fluid and a nuclear magnetic detection phase fluid are firstly selected, and the dead volume is filled with the displacing phase fluid and the core is saturated with the nuclear magnetic detection phase fluid. The nuclear magnetic resonance (NMR) T2 spectrum of the core to be measured in the above case is measured, that is, the calibrated T2 spectrum.

It can be understood that nuclear magnetic moments in the core to be measured are arranged irregularly and freely without any external field. Under the influence of a fixed uniform strong magnetic field, a spin system is polarized, and the nuclear magnetic moments are reoriented and aligned in the direction of the magnetic field. At the same time, there is an orbital moment of momentum around the nucleus, like a gyroscope, and the direction of the magnetic field precesses at a frequency, proportional to the strength of the magnetic field. In the polarized magnetic field, if an alternating magnetic field is applied in the direction perpendicular to the magnetic field and the frequency is also a precession frequency of the proton (hydrogen nucleus), the resonance absorption phenomenon, i.e. the nuclear magnetic moment in the low energy state, will occur. By absorbing the energy provided by the alternating magnetic field, it transitions to a high energy state, and such phenomenon is known as nuclear magnetic resonance.

A step 200 for measuring a nuclear magnetic resonance (NMR) T2 spectrum of a process in which the core to be measured is converted from a saturated displaced phase fluid into a displacing phase fluid to generate a displacement process T2 spectrum.

Similar to the step 100, the displacing phase fluid, the displaced phase fluid and the nuclear magnetic detection phase fluid are firstly selected, and next, the nuclear magnetic resonance (NMR) T2 spectrum of the core to be measured in the above case is measured, that is, the displacement process T2 spectrum.

A step 300 for generating the fluid saturation of the on-line displacement system in real time according to the calibrated T2 spectrum and the displacement process T2 spectrum.

The NMR transverse relaxation spectrum feeds back two aspects of information, one is the intensity of signal, which is proportional to the quantity of fluid, i.e., $$M = M_0 e^{-T_e/T_2} \quad (1)$$

Where, M denotes the observed NMR signal intensity, $M_0$ denotes a constant, proportional to the number of hydrogen nucleus, $T_e$ denotes the echo interval, $T_2$ denotes the transverse relaxation time, therefore, the signal intensity is proportional to the amount of fluid to be measured; the other information is the length of $T_2$, which is affected by surface relaxation, so that the larger the aperture is, the longer the relaxation time in $T_2$ spectrum is.

In implementation of the step 300, the core is completely saturated with one phase fluid that produces a NMR signal, the displacement process is loaded in which the NMR signal thereof is measured as a calibration standard under conditions similar to those of displacement, then the NMR signal measured in the actual displacement process is compared with the calibration standard, so as to obtain the corresponding saturation of the phase fluid:

$$S_i = \frac{\sum_0^{TD} L(T)}{\sum_0^{TD} L_{max}(T)} \times 100\% \quad (2)$$

the saturation of the fluid phase that does not produce the NMR signal is:

$$S_j = 1 - S_i \quad (3)$$

As can be seen from the above description, the embodiment of the present invention provides a method for measuring fluid saturation in nuclear magnetic resonance (NMR) on-line displacement, in which the critical filling pressure of gas displacement in low permeability core is determined by the change of the NMR signal in the process of gas injection.

Figure 4:
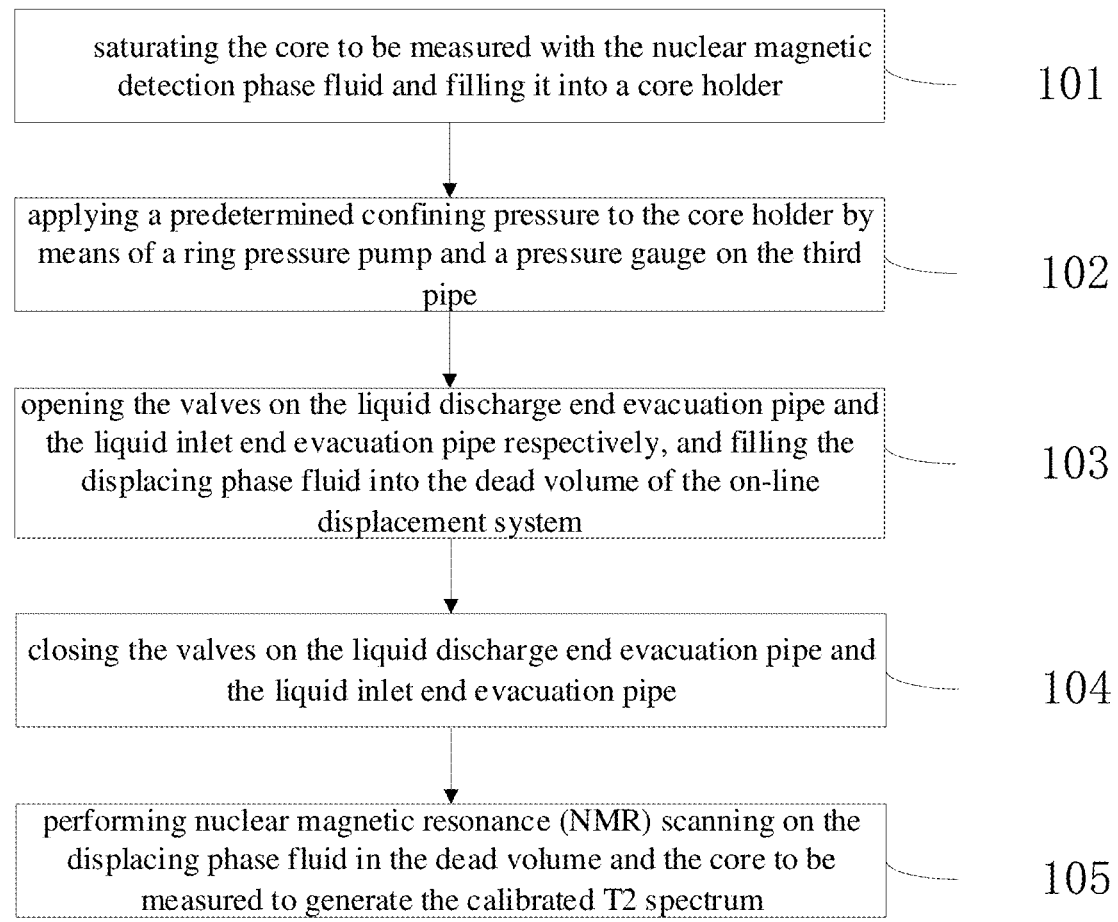
FIG. 4 is a flow schematic diagram of the step 100 of the method for measuring fluid saturation in nuclear magnetic resonance (NMR) on-line displacement according to an embodiment of the present invention.

In an embodiment, referring to FIG. 4, the step 100 further includes:

a step 101 for saturating the core to be measured with the nuclear magnetic detection phase fluid and filling it into a core holder;

a step 102 for applying a predetermined confining pressure to the core holder by means of a ring pressure pump and a pressure gauge on the third pipe;

a step 103 for opening the valves on the liquid discharge end evacuation pipe and the liquid inlet end evacuation pipe respectively, and filling the displacing phase fluid into the dead volume of the on-line displacement system;

a step 104 for closing the valves on the liquid discharge end evacuation pipe and the liquid inlet end evacuation pipe;

a step 105 for performing nuclear magnetic resonance (NMR) scanning on the displacing phase fluid in the dead volume and the core to be measured to generate the calibrated T2 spectrum.

In the steps 101 to 105, the core to be measured is saturated with the nuclear magnetic detection phase fluid after the core to be measured is dried until the weight does not change any more; the core is loaded into the core holder 1-6, a predetermined confining pressure is applied, the core holder injection end movable plug evacuation valve 1-4 is opened, and the dead volume is filled with displacing phase fluid, then the core holder injection end movable plug evacuation valve 1-4 is closed and the core holder liquid discharge end movable plug evacuation valve 1-8 is opened, the dead volume is filled with the fluid phase selected in Table 1, and the core holder liquid discharge end movable plug evacuation valve 1-8 is closed. Next, NMR scanning is performed on the core to be measured and the dead volume fluid to obtain the T2 spectrum $L_{max}$, that is, the calibrated T2 spectrum, of the phase fluid which is completely saturated to generate the NMR signal.

Figure 5:
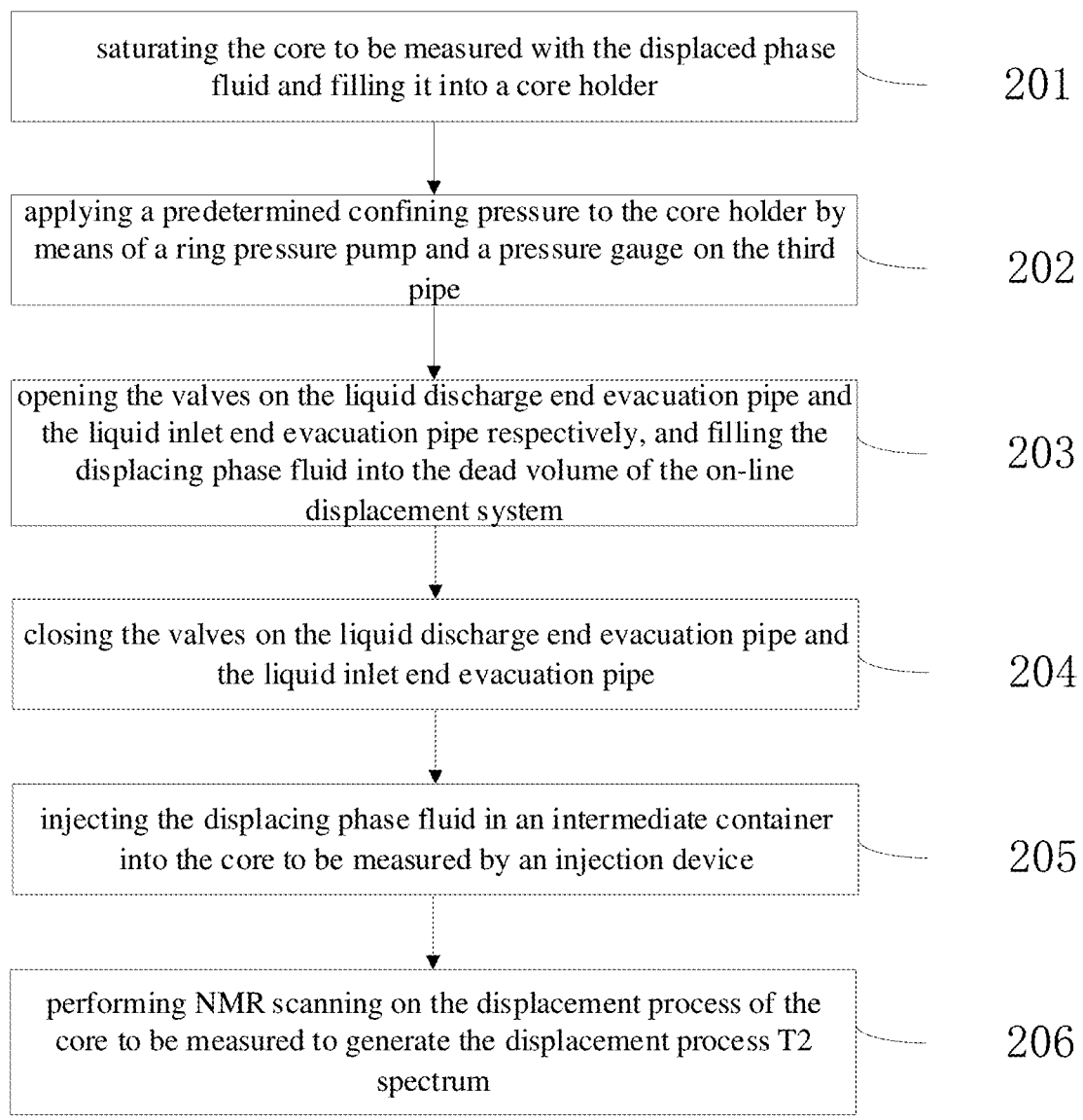
FIG. 5 is a flow schematic diagram of the step 200 of the method for measuring fluid saturation in nuclear magnetic resonance (NMR) on-line displacement according to an embodiment of the present invention.

In an embodiment, referring to FIG. 5, the step 200 further includes:
- a step 201 for saturating the core to be measured with the displaced phase fluid and filling it into a core holder;
- a step 202 for applying a predetermined confining pressure to the core holder by means of a ring pressure pump and a pressure gauge on the third pipe;
- a step 203 for opening the valves on the liquid discharge end evacuation pipe and the liquid inlet end evacuation pipe respectively, and filling the displacing phase fluid into the dead volume of the on-line displacement system;
- a step 204 for closing the valves on the liquid discharge end evacuation pipe and the liquid inlet end evacuation pipe;
- a step 205 for injecting the displacing phase fluid in an intermediate container into the core to be measured by an injection device;
- a step 206 for performing NMR scanning on the displacement process of the core to be measured to generate the displacement process T2 spectrum.

In the steps 201 to 206, the displacing phase fluid and the displaced phase fluid are firstly selected, and then the core to be measured is saturated with the displaced phase fluid; the core to be measured is loaded into the core holder 1-6, a predetermined confining pressure is applied, the core holder injection end movable plug evacuation valve 1-4 is opened, and the dead volume is filled with displacing phase fluid, then the core holder injection end movable plug evacuation valve 1-4 is closed and the core holder liquid discharge end movable plug evacuation valve 1-8 is opened, the core holder liquid discharge end pipeline and the dead volume are filled with the fluid phase selected in advance, and the core holder liquid discharge end movable plug evacuation valve 1-8 is closed; the injection pump 1-10 is used to inject the displacing phase fluid into one side of the piston in the intermediate container 1-3, and the displacing phase fluid on the other side of the piston is pressurized, the displacing phase fluid displaces the saturated displaced phase fluid in the core, the NMR scanning is continued until the observed T2 spectrum does not change, and the T2 spectrum $L_n$ of the serial displacement process is obtained, that is the displacement process T2 spectrum.

Figure 6:
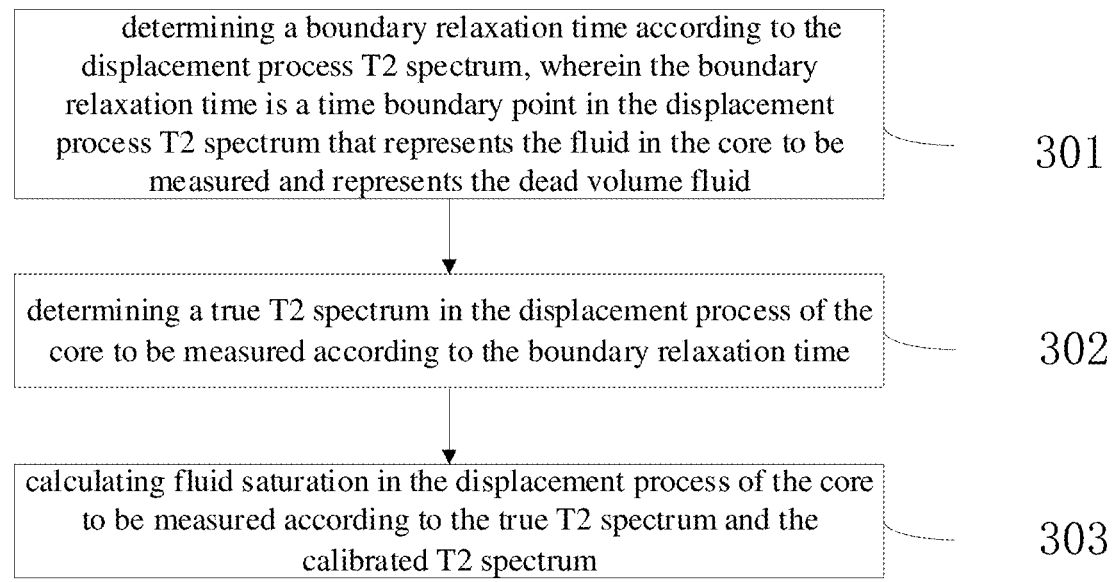
FIG. 6 is a flow schematic diagram of the step 300 of the method for measuring fluid saturation in nuclear magnetic resonance (NMR) on-line displacement according to an embodiment of the present invention.

In an embodiment, referring to FIG. 6, the step 300 further includes:

A step 301 for determining a boundary relaxation time according to the displacement process T2 spectrum, wherein the boundary relaxation time is a time boundary point in the displacement process T2 spectrum that represents the fluid in the core to be measured and represents the dead volume fluid.

It can be understood that in fact this boundary point is determined based on the displacement process T2 spectrum. For the same core, once the boundary point is determined, it is applicable to the calibrated T2 spectrum, the initial state T2 spectrum and the displacement process T2 spectrum.

A step 302 for determining a true T2 spectrum in the displacement process of the core to be measured according to the boundary relaxation time.

A step 303 for calculating fluid saturation in the displacement process of the core to be measured according to the true T2 spectrum and the calibrated T2 spectrum.

Figure 7:
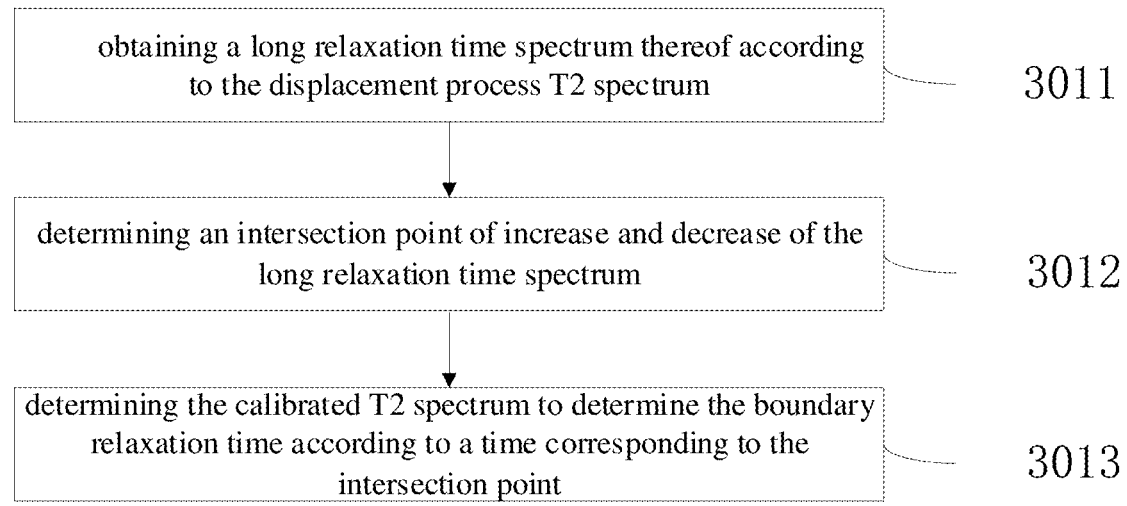
FIG. 7 is a flow schematic diagram of the step 301 of the method for measuring fluid saturation in nuclear magnetic resonance (NMR) on-line displacement according to an embodiment of the present invention.

In the steps 301 to 303, referring to FIG. 7, the characteristics of long relaxation time tending to the spectral line in T2 spectrum is observed and the intersection point where the signal amplitude increases and decreases in this region is determined, the relaxation time TD corresponding to this point is a boundary point between the saturated fluid and the dead volume fluid in T2 spectrum, and the signal with relaxation time less than TD is the NMR signal of core saturated fluid; then the fluid saturation in the displacement process of the core to be measured is calculated in real time according to the equation (2) and the equation (3).

In an embodiment, referring to FIG. 7, the step 301 further includes:
- A step 3011 for obtaining a long relaxation time spectrum thereof according to the displacement process T2 spectrum;
- A step 3012 for determining an intersection point of increase and decrease of the long relaxation time spectrum;
- A step 3013 for determining the calibrated T2 spectrum to determine the boundary relaxation time according to a time corresponding to the intersection point.

In an embodiment, referring to FIG. 8, the method for measuring fluid saturation in nuclear magnetic resonance (NMR) on-line displacement further comprises:
- A step 400 for measuring a nuclear magnetic resonance (NMR) T2 spectrum under the dead volume filling of the on-line displacement system as displacing phase fluid and the core to be measured that is saturated with the displaced phase fluid, to generate an initial T2 spectrum;
- A step 500 for correcting the fluid saturation of the on-line displacement system according to the initial T2 spectrum, the calibrated T2 spectrum and the displacement process T2 spectrum.

In the steps 400 and 500, the equation (2) is modified to account for the effects of the core holder injection end pipeline and the dead volume fluid NMR signal and background noise, and the corresponding saturation of the fluid generating the NMR signal at different time is calculated according to the following equation:

$$S_i(n) = \frac{\sum_0^{TD} L(T) - \sum_0^{TD} L_0(T)}{\sum_0^{TD} L_{max}(T) - \sum_0^{TD} L_0(T)} \times 100\% \quad (4)$$

the saturation of the fluid phase that does not produce the NMR signal is:

$$S_j(n) = 1 - S_i(n) \quad (5)$$

In an embodiment, referring to FIG. 9, the step 400 further includes:
- a step 401 for saturating the core to be measured with the displaced phase fluid and filling it into a core holder;
- a step 402 for applying a predetermined confining pressure to the core holder by means of a ring pressure pump and a pressure gauge on the third pipe;
- a step 403 for opening the valves on the liquid discharge end evacuation pipe and the liquid inlet end evacuation pipe respectively, and filling the displacing phase fluid into the dead volume of the on-line displacement system;
- a step 404 for closing the valves on the liquid discharge end evacuation pipe and the liquid inlet end evacuation pipe;
- a step 405 for performing nuclear magnetic resonance (NMR) scanning on the displacing phase fluid in the dead volume and the core to be measured to generate the initial T2 spectrum.

In the above steps, the displacing phase fluid and the displaced phase fluid are firstly selected, and then the core to be measured is saturated with the displaced phase fluid; the core to be measured is loaded into the core holder 1-6, a predetermined confining pressure is applied, the core holder injection end movable plug evacuation valve 1-4 is opened, and the dead volume is filled with displacing phase fluid, then the core holder injection end movable plug evacuation valve 1-4 is closed and the core holder liquid discharge end movable plug evacuation valve 1-8 is opened, the core holder liquid discharge end pipeline and the dead volume are filled with the fluid phase selected in Table 1, and the core holder liquid discharge end movable plug evacuation valve 1-8 is closed; NMR scanning is performed on the core to be measured, the injection end and the liquid discharge end pipeline and the dead volume fluid, so as to obtain the initial $L_0$.

In order to further illustrate the scheme, the invention further provides a specific application example of the method for measuring fluid saturation in nuclear magnetic resonance (NMR) on-line displacement.

In this specific application example, the invention further comprises a device for measuring fluid saturation in nuclear magnetic resonance (NMR) on-line displacement. Referring to FIGS. 1 and 2, the device comprises:

an injection pump 1-1, a liquid inlet end pressure gauge 1-2, an intermediate container 1-3, a core holder 1-6, a core holder liquid inlet end evacuation valve 1-4; a core holder liquid discharge end evacuation valve 1-8; a confining pressure gauge 1-7, a confining pressure valve 1-9 and a confining pressure pump 1-10.

The structure of the core holder includes a sleeve 2-1, a confining pressure interface 2-2, a fixed plug 2-4, a movable plug 5-5, a liquid discharge end movable plug evacuation pipe 2-6, a liquid discharge end movable plug liquid discharge pipe 2-7, an O-shaped sealing ring 2-8, a rubber pipe 2-9, a liquid inlet end movable plug liquid inlet pipe 2-10, a liquid inlet end movable plug evacuation pipe 2-11; and a liquid inlet end movable plug 2-12. In order to prevent the measurement result from being affected by the NMR signal generated by the rubber pipe, the rubber pipe 2-9 is made of a high-purity fluorine rubber material. In the core holder, the cavity surrounded by the two-end fixed plug 2-4, the sleeve 2-1 and the rubber pipe 2-9 is called the confining pressure cavity.

The NMR measurement sub-system includes magnets 1-5, between two of which a uniform static magnetic field is provided, radio frequency coil 2-3. Other NMR devices and control devices are not listed as general purpose devices.

In addition, in order to improve the signal-to-noise ratio of the nuclear magnetic resonance measurement, the radio frequency coil is built in a confinement pressure cavity of the core holder. In order to prevent the measurement effect from being affected by the nuclear magnetic resonance signal generated by the fluid in the confining pressure cavity, the fluid used for filling the confining pressure cavity is fluorocarbon oil without the NMR signal. In order to ensure that the core holder has sufficient strength and does not produce interference to the NMR signal, the high-purity non-magnetic steel is used for making the core holder.

In the prior art, there are two main problems when the fluid saturation of the nuclear magnetic resonance (NMR) on-line displacement system is measured:
1) different fluid NMR signals may overlap on the T2 spectrum;
2) dead volume fluid brings a system error.

For the problem that immiscible two phase fluid signals overlap, only one of the first phase fluid and the second phase fluid can produce a NMR signal by proper operation. In particular, during oil-water two-phase displacement, heavy water is selected or divalent manganese ions are added into the water (concentration of the manganese ions >=700 mg/L), such that the water phase does not generate NMR signals, and NMR signal measurement is performed only on the oil phase, thereby avoiding the problem that two phase fluid NMR signals overlap. For the system error caused by the dead volume fluid signal, considering that the size of the diversion trench of the core holder movable plug and the inner diameter of the pipeline in the magnetic field is obviously larger than that of the rock pore, the corresponding transverse relaxation time of the dead volume fluid is obviously larger than that of pore fluid. On the T2 spectrum, there is a boundary relaxation time TD (FIG. 10), below which the T2 spectrum reflects the signal of the core saturated fluid, and above which the T2 spectrum reflects the fluid signal of the dead volume. In calculation of the fluid saturation, the influence on saturation measurement caused by the dead volume fluid can be eliminated only by counting the portion of signals whose relaxation time is less than TD.

In particular, prior to the experiment, the dead volume of the liquid discharge end movable plug of the core holder is previously filled with the selected fluid phase, according to the scenario set forth in Table 1. It can be observed in the displacement process that the NMR signal corresponding to dead volume fluid increases at first and then decreases, or decreases at first and then increases. The relaxation time corresponding to the intersection point of the T2 spectrum at the time of increasing and the T2 spectrum at the time of decreasing is TD.

TABLE 1

Comparison Table of Displacement Scenarios

| Serial No.: | Displacing phase | Displaced phase | Dead volume saturated fluid phase at the outlet end of the holder | Nuclear magnetic detection fluid phase | Increasing and decreasing trend of the NMR signal of the dead volume fluid |
|---|---|---|---|---|---|
| 1 | oil | water | oil | oil | decrease at first and then increase |
| 2 | water | oil | water | oil | increase at first and then decrease |
| 3 | gas | water | gas | water | increase at first and then decrease |
| 4 | water | gas | water | water | decrease at first and then increase |

TABLE 1-continued

Comparison Table of Displacement Scenarios

| Serial No.: | Displacing phase | Displaced phase | Dead volume saturated fluid phase at the outlet end of the holder | Nuclear magnetic detection fluid phase | Increasing and decreasing trend of the NMR signal of the dead volume fluid |
|---|---|---|---|---|---|
| 5 | gas | oil | gas | oil | increase at first and then decrease |
| 6 | oil | gas | oil | oil | decrease at first and then increase |

Here the principle of fluid change and signal increasing trend at the liquid discharge end of NMR on-line displacement is explained by taking oil displacing water as an example. In FIGS. 11 to 16, 4-1 denotes a nuclear magnetic resonance (NMR) magnet, 4-2 denotes a core holder liquid discharge end movable plug evacuation valve, 4-3 denotes a core holder liquid discharge end movable plug, 4-4 denotes a dead volume, 4-5 denotes a core, 4-6 denotes a direction of displacement.

Figure 10:
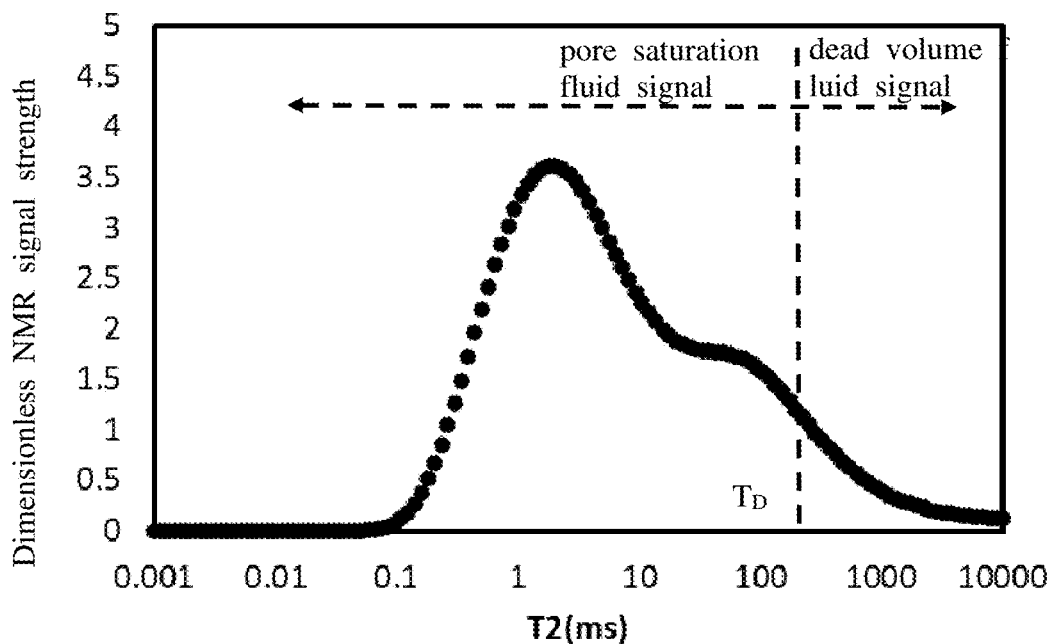
FIG. 10 is a schematic diagram of a nuclear magnetic resonance (NMR) T2 spectrum and boundary relaxation time TD according to an embodiment of the present invention.
Figure 11:
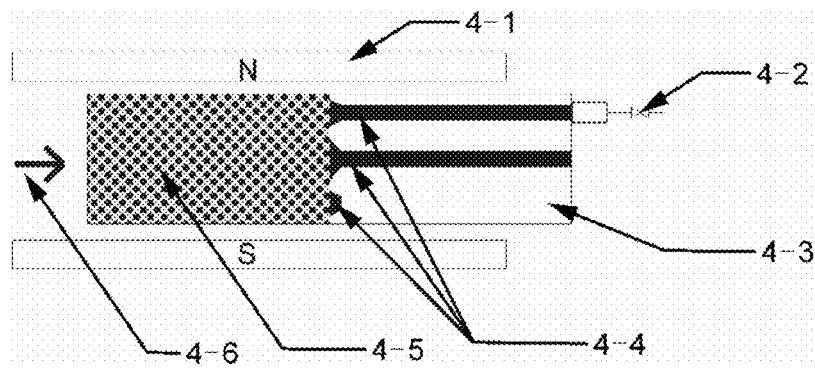
FIG. 11 is the first schematic diagram of the trends of fluid change and signal increase at the liquid discharge end of the nuclear magnetic resonance on-line displacement device in the specific application example of the present invention.
Figure 12:
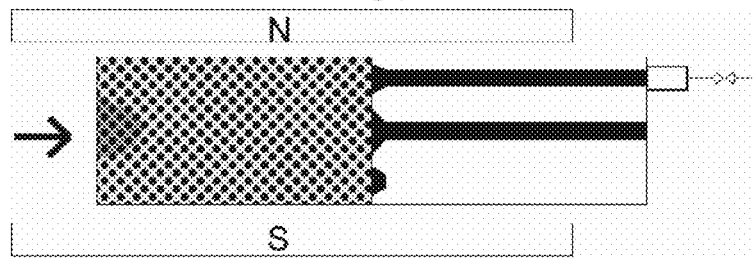
FIG. 12 is the second schematic diagram of the trends of fluid change and signal increase at the liquid discharge end of the nuclear magnetic resonance on-line displacement device in the specific application example of the present invention.
Figure 13:
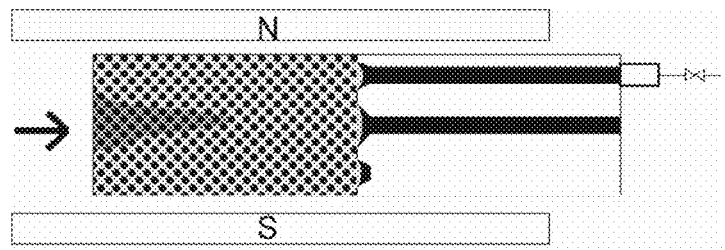
FIG. 13 is the third schematic diagram of the trends of fluid change and signal increase at the liquid discharge end of the nuclear magnetic resonance on-line displacement device in the specific application example of the present invention.
Figure 14:
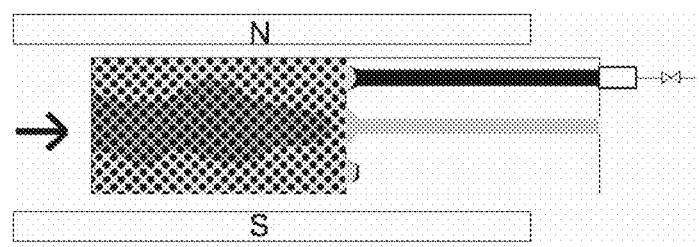
FIG. 14 is the fourth schematic diagram of the trends of fluid change and signal increase at the liquid discharge end of the nuclear magnetic resonance on-line displacement device in the specific application example of the present invention.
Figure 15:
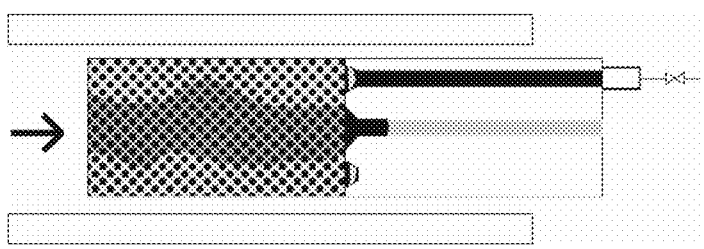
FIG. 15 is the fifth schematic diagram of the trends of fluid change and signal increase at the liquid discharge end of the nuclear magnetic resonance on-line displacement device in the specific application example of the present invention.
Figure 16:
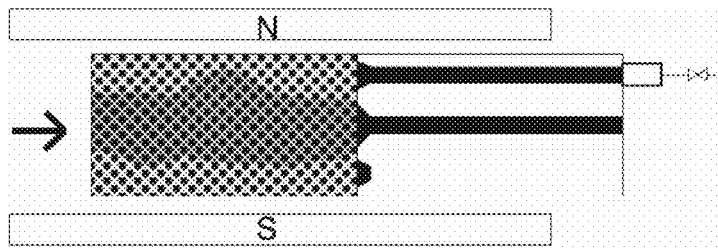
FIG. 16 is the sixth schematic diagram of the trends of fluid change and signal increase at the liquid discharge end of the nuclear magnetic resonance on-line displacement device in the specific application example of the present invention.

In FIG. 10, in the initial state, the core is saturated the water phase (manganese water or heavy water), the corresponding dead volume and pipeline at the core holder liquid discharge end plug are filled with oil phase. In FIG. 11, when the oil starts to enter the core, but the pressure wave is not transmitted to the core liquid discharge end, the core does not discharge liquid, the NMR signal in the core is increased, and the NMR signal of the dead volume fluid is unchanged. In FIG. 12, when the core liquid discharge end starts to discharge water, the dead volume oil phase is discharged out of the effective magnetic field region, and the NMR signal of the dead volume fluid is gradually weakened. In FIG. 13, the core liquid discharge end continues to discharge water, the oil phase is continuously discharged from the dead volume, and the NMR signal corresponding to the dead volume reaches the minimum value. In FIG. 14, the core liquid discharge end starts to discharge oil, and the NMR signal corresponding to the dead volume continuously increases. In FIG. 15, finally, the dead volume of the core liquid drainage end is refilled with oil, and the corresponding signal reaches the maximum value.

Figure 17:
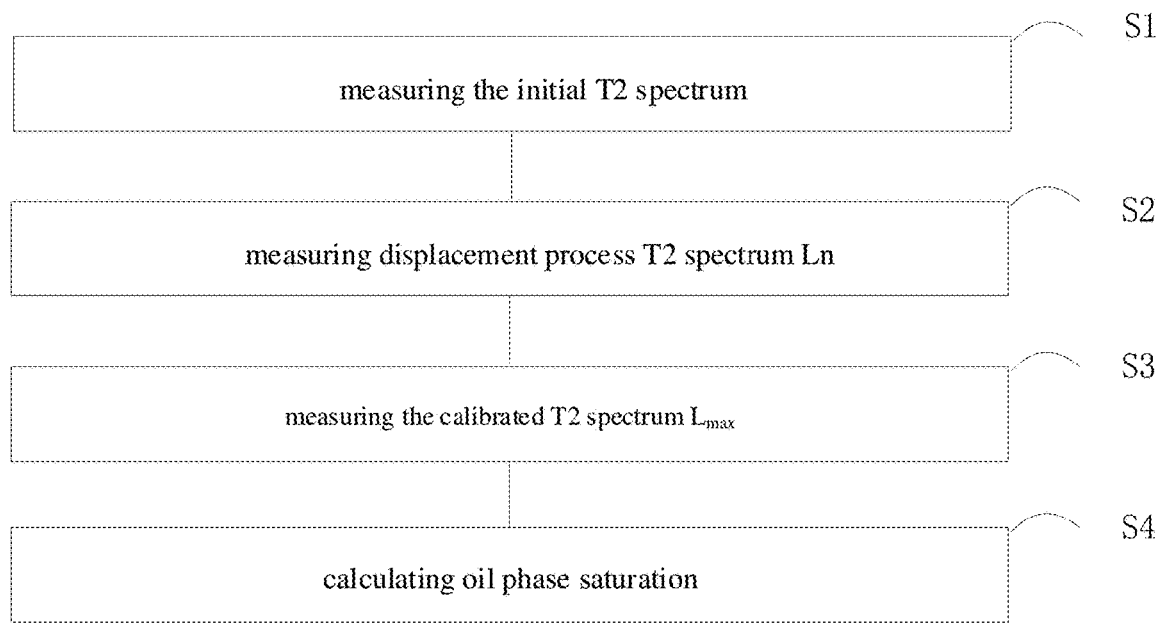
FIG. 17 is a flow schematic diagram of the method for measuring fluid saturation in nuclear magnetic resonance (NMR) on-line displacement in the specific application example of the present invention.

Referring to FIG. 17, based on the above described device for measuring fluid saturation in nuclear magnetic resonance (NMR) on-line displacement and the above analysis, the method for measuring fluid saturation in nuclear magnetic resonance (NMR) on-line displacement provided in the specific application example comprises the following steps (taking the core ZO4 as an example):

In this specific application example, the magnetic field strength of the used nuclear magnetic resonance is 0.23T, the main frequency of the corresponding hydrogen resonance is 10.11 MHz. In measurement, the echo interval is TE=200 us, and the waiting time is TR=3000 ms.

The oil saturation of the core ZO4 is analyzed during the filling process. The core diameter is D=25.23 mm, the length is L=45.30 mm, the porosity=10.40%, the permeability K=1.034 mD.

The phase fluid used in the injection pump is distilled water, and the displacing phase fluid is neutral kerosene, which are used as nuclear magnetic resonance detection fluid phase. The displaced phase fluid is heavy water (No NMR signal is generated).

S1: Measuring the Initial T2 Spectrum.

The core ZO4 is saturated with heavy water of the displaced phase fluid; the core is loaded into the core holder and a predetermined confining pressure of 20 MPa is applied, the core holder injection end movable plug evacuation valve is opened, and the core holder injection end pipeline and the dead volume are filled with neutral kerosene, then the core holder injection end movable plug evacuation valve is closed and the core holder liquid discharge end movable plug evacuation valve is opened, the core holder liquid discharge end pipeline and the dead volume are also filled with neutral kerosene, and the core holder liquid discharge end movable plug evacuation valve is closed. The NMR scanning is performed on the saturated core, the injection end and the liquid discharge end pipeline and the dead volume fluid, so as to obtain the initial T2 spectrum $L_0$.

S2: Measuring Displacement Process T2 Spectrum $L_n$.

Distilled water is injected into the intermediate container with an injection pump at a flow rate of 0.1 ml/min, the neutral kerosene on the other side of the piston of the intermediate container is pressurized, and the neutral kerosene displaces the saturated heavy water in the core. The NMR scanning is continued until the observed T2 spectrum does not change, and a series of displacement process T2 spectrum $L_n$ is obtained.

S3: Measuring the Calibrated T2 Spectrum $L_{max}$.

Figure 18:
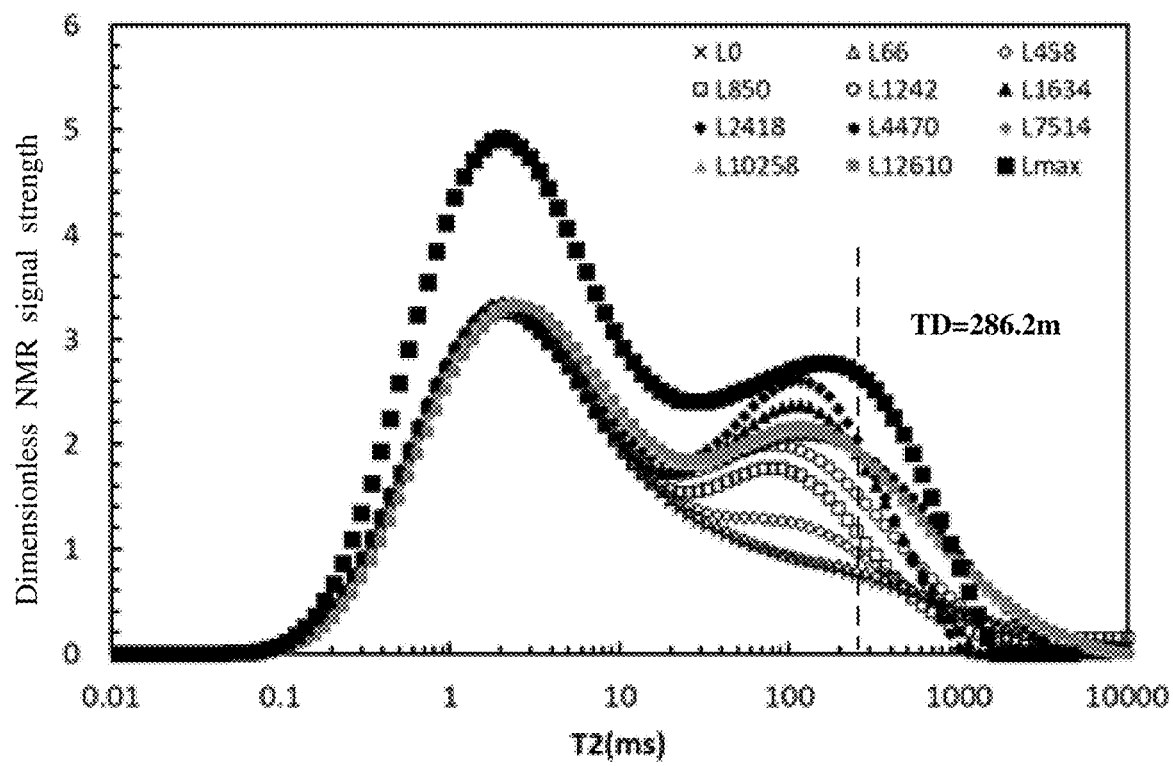
FIG. 18 is a schematic diagram of determining TD boundary value of ZO4 core in the specific application example of the present invention.

The core is firstly taken out of the holder and dried until the weight does not change any more and the neutral kerosene is completely saturated; the core is loaded into the core holder again and a predetermined confining pressure is applied, the core holder injection end movable plug evacuation valve is opened, and the core holder injection end pipeline and the dead volume are filled with neutral kerosene, then the core holder injection end movable plug evacuation valve is closed and the core holder liquid discharge end movable plug evacuation valve is opened, the core holder liquid discharge end pipeline and the dead volume are filled with neutral kerosene, and the core holder liquid discharge end movable plug evacuation valve is closed. The NMR scanning is performed on the saturated core, the injection end and the liquid discharge end pipeline and the dead volume fluid, so as to obtain the T2 spectrum $L_{max}$ at the time of being completely saturated with neutral kerosene. A characteristic that that the characteristics of long relaxation time tending to the spectral line in T2 spectrum is observed and the intersection point where the signal amplitude increases and decreases in this region is determined (referring to FIG. 18, the signal corresponding to the dead volume fluid has two changing trends of increasing and decreasing in the displacement process, and the relaxation time at the intersection point of the two is the boundary relaxation time TD between the saturated fluid and the dead volume fluid), the relaxation time TD corresponding to this point is a boundary point between the saturated fluid and the dead volume fluid in T2 spectrum, and the signal with relaxation time less than TD is the NMR signal of core saturated fluid.

S4: Calculating Oil Phase Saturation.

Figure 19:
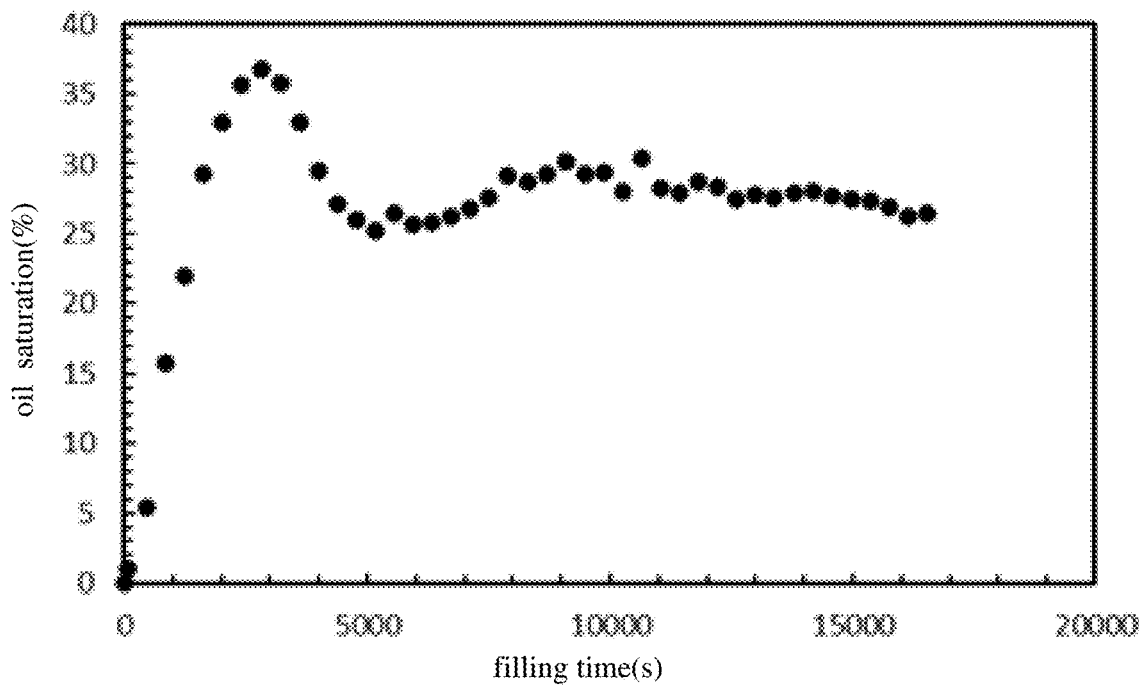
FIG. 19 is a schematic diagram of calculating oil saturation in the process of ZO4 core filling in the specific application example of the present invention.

The oil phase saturation $S_i(n)$ in the filling process is calculated by using the equation (4), and the corresponding heavy water saturation is $S_j(n)=1-S_i(n)$. The measurement result of oil saturation of core ZO4 during filling is shown in FIG. 19.

As can be seen from the above description, the embodiment of the present invention provides a device and a method for measuring fluid saturation in nuclear magnetic resonance (NMR) on-line displacement, the method comprising: measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum; measuring a nuclear magnetic resonance (NMR) T2 spectrum of a process in which the core to be measured is converted from a saturated displaced phase fluid into a displacing phase fluid to generate a displacement process T2 spectrum; generating the fluid saturation of the on-line displacement system in real time according to the generated calibrated T2 spectrum and the displacement process T2 spectrum. In the present invention, the boundary point between the saturated fluid and the dead volume fluid in T2 spectrum is determined by observing the change characteristics of the T2 spectrum, so that only the saturated fluid signal can be counted, and the influence of the dead volume fluid can be shielded, so as to improve measurement precision of fluid saturation in the on-line displacement process.

The embodiment of the invention provides an electronic device, which can be a desktop computer, a tablet computer, a mobile terminal, etc. The embodiment is not limited to this.

Figure 20:
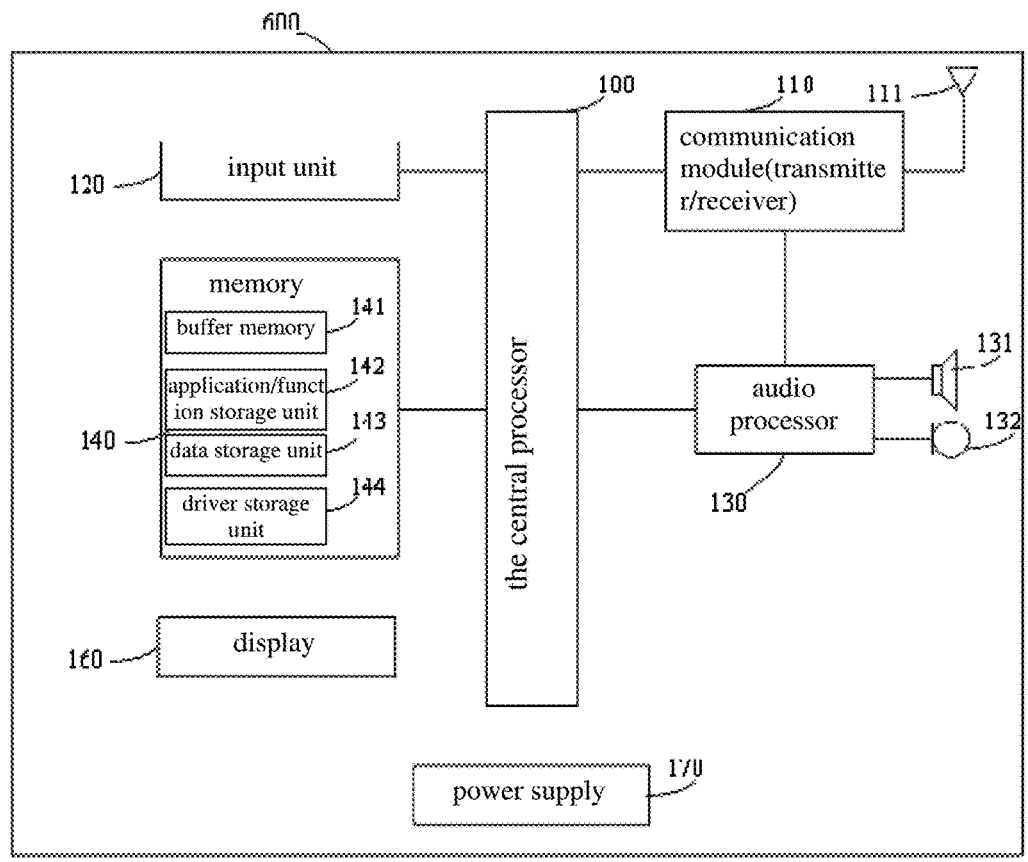
FIG. 20 is a schematic block diagram of the system configuration of the electronic device 600 according to the embodiment of the present invention.

FIG. 20 is a schematic block diagram of the system configuration of the electronic device 600 according to the embodiment of the present invention. As shown in FIG. 20, the electronic device 600 may include a central processor 100 and a memory 140; The memory 140 is coupled to the central processor 100. It is worth noting that the figure is exemplary; Other types of structures can also be used to supplement or replace the structure to realize telecommunication functions or other functions.

In one embodiment, the online displacement fluid saturation measurement function can be integrated into the central processor 100. Wherein, the central processor 100 can be configured to control the following: measure the nuclear magnetic resonance T2 spectrum under the condition that the dead volume of the online displacement system is filled with displacement phase fluid and the core to be measured is saturated nuclear magnetic detection phase fluid to generate calibrated T2 spectrum; Measure the NMR T2 spectrum of the process of the measured core changing from saturated displacement phase fluid to displacement phase fluid to generate the T2 spectrum of the displacement process; According to the calibrated T2 spectrum and the T2 spectrum of the displacement process, the online displacement system fluid saturation is generated in real time.

In another embodiment, the online displacement fluid saturation measurement device can be configured separately from the central processor 100. For example, the online displacement fluid saturation measurement device can be configured as a chip connected to the central processor 100, and the online displacement fluid saturation measurement function can be realized through the control of the central processor.

As shown in FIG. 20, the electronic device 600 can also include a communication module 110, an input unit 120, an audio processor 130, a display 160, and a power supply 170. It is worth noting that the electronic device 600 does not have to include all the components shown in FIG. 20; In addition, the electronic device 600 may also include components not shown in FIG. 20, and the prior art may be referred to.

As shown in FIG. 20, the central processor 100, sometimes referred to as a controller or an operation control, may include a microprocessor or other processor device and/or a logic device, which receives inputs and controls the operation of various components of the electronic device 600.

The memory 140, for example, can be one or more of buffers, flash memory, hard drives, removable media, volatile memory, non-volatile memory, or other suitable devices. The above information related to the failure can be stored, and the program for executing the information can also be stored. And the central processor 100 may execute the program stored in the memory 140 to realize information storage, processing, and the like.

The input unit 120 provides input to the central processor 100. The input unit 120 is, for example, a key or touch input device. The power supply 170 is used to provide power to the electronic device 600. The display 160 is used for displaying display objects such as images and text. The display may be, for example, an LCD display, but is not limited thereto.

The memory 140 may be a solid-state memory, for example, a read-only memory (ROM), a random access memory (RAM), a SIM card, and the like. It can also be a memory that stores information even when power is off, can be selectively erased, and has more data. Examples of this memory are sometimes referred to as EPROMs. The memory 140 may also be some other type of device. The memory 140 includes a buffer memory 141 (sometimes referred to as a buffer). The memory 140 may include an application/function storage unit 142 for storing application programs and function programs or for executing the operation of the electronic device 600 through the central processor 100.

The memory 140 may also include a data storage unit 143 for storing data, such as contacts, digital data, pictures, sounds, and/or any other data used by electronic devices. The driver storage unit 144 of the memory 140 may include various drivers for the communication function of the electronic device and/or for performing other functions of the electronic device, such as a messaging application, an address book application, and the like.

The communication module 110 is a transmitter/receiver 110 that transmits and receives signals via the antenna 111. The communication module (transmitter/receiver) 110 is coupled to the central processor 100 to provide an input signal and receive an output signal, which may be the same as in the case of a conventional mobile communication terminal.

Based on different communication technologies, multiple communication modules 110 can be set in the same electronic device, such as cellular network module, Bluetooth module and/or wireless LAN module. The communication module (transmitter/receiver) 110 is also coupled to the speaker 131 and the microphone 132 via the audio processor 130 to provide audio output via the speaker 131, and to receive audio input from the microphone 132, thereby realizing normal telecommunication functions. The audio processor 130 may include any suitable buffer, decoder, amplifier, and the like. In addition, the audio processor 130 is also coupled to t the central processor 100, so that the sound can be recorded on the local unit through the microphone 132, and the sound stored on the local unit can be played through the speaker 131.

Specific embodiments of the present specification have been described in the above. Other embodiments fall within the scope of the appended claims. In some cases, the actions or steps recited in the claims may be performed in a different order from that in the embodiments and still achieve the desired results. In addition, the processes depicted in the drawings do not necessarily require a particular order or a sequential order shown in order to achieve the desired results.

Although the embodiment of the specifications provides the method operation steps as described in the embodiment or the flowcharts, more or less operation steps may be included based on the conventional or non-creative means. The order of the steps listed in the embodiments is merely one of various execution orders of the steps, rather than a unique execution order. At an actual apparatus or a terminal product, the steps may be performed in sequence or in parallel according to the methods illustrated in the embodiments or drawings (e.g., by a parallel processor or under a multi-threaded processing environment and even a distributed data processing environment). The term "comprise", "include" or any other variant intends to cover the non-exclusive inclusions, so that a process, a method, a commodity or a device comprising a series of elements comprise not only those elements, but also other elements not explicitly listed, or further comprise inherent elements of such process, method, commodity or device. In a case where there is no further limitation, it does not exclude other identical elements existing in the process, method, commodity or device comprising the elements.

The various embodiments in the specification are described in a progressive manner, and the same or similar parts between the various embodiments may be referred to each other, and each embodiment focuses on the differences from the other embodiments. In particular, the system embodiment is simply described since it is substantially similar to the method embodiment, and please refer to the description of the method embodiment for the relevant content.

The above description is merely an example of the embodiment of the present specification, and is not intended to limit the embodiment of the present specification. Various modifications and variations may be made to the embodiments of the present specification by those skilled in the art. Any modifications, equivalents, improvements, etc. made within the spirit and principle of the embodiments of the present specification shall be included within the scope of the claims of the embodiments of the present specification.

What is claimed is:

1. A method for measuring fluid saturation in on-line displacement applied to a device for measuring fluid saturation in nuclear magnetic resonance (NMR) on-line displacement, characterized in comprising:

measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum;

measuring a nuclear magnetic resonance (NMR) T2 spectrum of a process in which the core to be measured is converted from a saturated displaced phase fluid into a displacing phase fluid to generate a displacement process T2 spectrum;

generating the fluid saturation of the on-line displacement system in real time according to the calibrated T2 spectrum and the displacement process T2 spectrum, wherein, the dead volume is the sum of the space of a liquid discharge end evacuation pipe, a liquid discharge end liquid discharge pipe, a liquid inlet end evacuation pipe, a liquid inlet end liquid inlet pipe and the space of the diversion trench of the core holder plug;

the nuclear magnetic detection phase fluid is a phase fluid in which the influence of the nuclear magnetic resonance is difficult to eliminate, among the displacing phase fluid and the displaced phase fluid;

the device for measuring fluid saturation in nuclear magnetic resonance (NMR) on-line displacement, comprising: an injection device, an intermediate container, a core holder, and a nuclear magnetic resonance (NMR) instrument, wherein, the injection device is connected to one end of the intermediate container through a first pipe, for injecting fluid into the intermediate container;

the other end of the intermediate container is connected to the core holder by a second pipe, for injecting the fluid into the core in the core holder;

the core holder is located in a central area of the magnetic field of the NMR instrument, for monitoring the NMR signal of the core to be measured;

the core holder includes a sleeve, two fixed plugs, a liquid discharge end movable plug and a liquid inlet end movable plug, wherein, the two fixed plugs are arranged at two ends of the sleeve respectively;

the liquid discharge end movable plug and the liquid inlet end movable plug pass through the fixed plugs and abut against both ends of the core, to fix the core axially;

the liquid discharge end movable plug is provided with an evacuation pipe and a liquid discharge pipe;

the liquid inlet end movable plug is provided with an evacuation pipe and a liquid inlet pipe;

the liquid inlet pipe is connected to the intermediate container through the second pipe.

2. The method for measuring fluid saturation in nuclear magnetic resonance (NMR) on-line displacement according to claim 1, characterized in that, the measuring a nuclear magnetic resonance (NMR) T2 spectrum under the dead volume filling of the on-line displacement system as displacing phase fluid and the core to be measured as saturated nuclear magnetic detection phase fluid to generate a calibrated T2 spectrum, includes:

saturating the core to be measured with the nuclear magnetic detection phase fluid and filling it into the core holder;

applying a predetermined confining pressure to the core holder by means of a ring pressure pump and a pressure gauge on the third pipe;

opening the valves on the liquid discharge end evacuation pipe and the liquid inlet end evacuation pipe respectively, and filling the displacing phase fluid into the dead volume of the on-line displacement system;

closing the liquid inlet end evacuation pipe and the valves on the liquid discharge end evacuation pipe;

performing nuclear magnetic resonance (NMR) scanning on the displacing phase fluid in the dead volume and the core to be measured to generate the calibrated T2 spectrum.

3. The method for measuring fluid saturation in nuclear magnetic resonance (NMR) on-line displacement according to claim 1, characterized in that, the measuring a nuclear magnetic resonance (NMR) T2 spectrum of a process in which the core to be measured is converted from a saturated displaced phase fluid into a displacing phase fluid to generate a displacement process T2 spectrum, includes:

saturating the core to be measured with the displaced phase fluid and filling it into the core holder;

applying a predetermined confining pressure to the core holder by means of a ring pressure pump and a pressure gauge on the third pipe;

opening the valves on the liquid discharge end evacuation pipe and the liquid inlet end evacuation pipe respectively, and filling the displacing phase fluid into the dead volume of the on-line displacement system;

closing the valves on the liquid discharge end evacuation pipe and the liquid inlet end evacuation pipe;

injecting the displacing phase fluid in the intermediate container into the core to be measured by an injection device;

performing NMR scanning on the displacement process of the core to be measured to generate the displacement process T2 spectrum.

4. The method for measuring fluid saturation in nuclear magnetic resonance (NMR) on-line displacement according to claim 1, characterized in that, the generating the fluid saturation of the on-line displacement system in real time according to the calibrated T2 spectrum and the displacement process T2 spectrum, includes:

determining a boundary relaxation time according to the displacement process T2 spectrum, wherein the boundary relaxation time is a time boundary point in the displacement process T2 spectrum that represents the fluid in the core to be measured and represents the dead volume fluid;

determining a true T2 spectrum in the displacement process of the core to be measured according to the boundary relaxation time;

calculating fluid saturation in the displacement process of the core to be measured according to the true T2 spectrum and the calibrated T2 spectrum.

5. The method for measuring fluid saturation in nuclear magnetic resonance (NMR) on-line displacement according to claim 4, characterized in that, the determining a boundary relaxation time according to the displacement process T2 spectrum, includes:

obtaining a long relaxation time spectrum thereof according to the displacement process T2 spectrum;

determining an intersection point of increase and decrease of the long relaxation time spectrum;

determining the calibrated T2 spectrum to determine the boundary relaxation time according to a time corresponding to the intersection point.

6. The method for measuring fluid saturation in nuclear magnetic resonance (NMR) on-line displacement according to claim 1, characterized in further comprising: correcting the fluid saturation of the on-line displacement system, including:

measuring a nuclear magnetic resonance (NMR) T2 spectrum under the dead volume filling of the on-line displacement system as displacing phase fluid and the core to be measured that is saturated with the displaced phase fluid, to generate an initial T2 spectrum;

correcting the fluid saturation of the on-line displacement system according to the initial T2 spectrum, the calibrated T2 spectrum and the displacement process T2 spectrum.

7. The method for measuring fluid saturation in nuclear magnetic resonance (NMR) on-line displacement according to claim 6, characterized in that, the measuring a nuclear magnetic resonance (NMR) T2 spectrum under the dead volume filling of the on-line displacement system as displacing phase fluid and the core to be measured that is saturated with the displaced phase fluid, to generate an initial T2 spectrum, includes:

saturating the core to be measured with the displaced phase fluid and filling it into a core holder;

applying a predetermined confining pressure to the core holder by means of a ring pressure pump and a pressure gauge on the third pipe;

opening the valves on the liquid discharge end evacuation pipe and the liquid inlet end evacuation pipe respectively, and filling the displacing phase fluid into the dead volume of the on-line displacement system;

closing the valves on the liquid discharge end evacuation pipe and the liquid inlet end evacuation pipe;

performing nuclear magnetic resonance (NMR) scanning on the displacement phase fluid in the dead volume and the core to be measured to generate the initial T2 spectrum.

\* \* \* \* \*